United States Patent [19]
Kamei et al.

[11] Patent Number: 5,668,111
[45] Date of Patent: *Sep. 16, 1997

[54] SUSTAINED-RELEASE PREPARATION

[75] Inventors: Shigeru Kamei, Takarazuka; Yasutaka Igari, Kobe; Yasuaki Ogawa, Ohyamazaki-cho, all of Japan

[73] Assignee: Takeda Chemical Industries, Ltd., Osaka, Japan

[ * ] Notice: The term of this patent shall not extend beyond the expiration date of Pat. No. 5,480,868.

[21] Appl. No.: 471,382

[22] Filed: Jun. 6, 1995

Related U.S. Application Data

[62] Division of Ser. No. 162,698, Dec. 7, 1993, Pat. No. 5,480,868.

[30] Foreign Application Priority Data

| Dec. 7, 1992 | [JP] | Japan | 4-327070 |
| Feb. 5, 1993 | [JP] | Japan | 5-108978 |
| Jun. 16, 1993 | [JP] | Japan | 5-145134 |

[51] Int. Cl.$^6$ ............................ A61K 38/00; C08G 63/08
[52] U.S. Cl. ...................... 514/15; 424/78.08; 424/78.33; 525/415; 528/354
[58] Field of Search ............................ 514/15; 424/78.08, 424/78.23; 528/354; 525/415

[56] References Cited

U.S. PATENT DOCUMENTS

| 3,773,919 | 11/1973 | Boswell et al. | 424/19 |
| 4,341,767 | 7/1982 | Nestor et al. | 424/177 |
| 5,036,047 | 7/1991 | Mia | 514/15 |
| 5,110,904 | 5/1992 | Haviv et al. | 530/313 |
| 5,140,009 | 8/1992 | Haviv et al. | 514/16 |
| 5,171,835 | 12/1992 | Janaky et al. | 530/313 |
| 5,187,150 | 2/1993 | Speiser et al. | 514/2 |
| 5,480,868 | 1/1996 | Kamei et al. | 514/15 |

FOREIGN PATENT DOCUMENTS

| 0 052 510 | 5/1982 | European Pat. Off. . |
| 0 058 481 | 8/1982 | European Pat. Off. . |
| 0 172 636 | 2/1986 | European Pat. Off. . |
| 0 182 262 | 5/1986 | European Pat. Off. . |
| 0 302 582 | 2/1989 | European Pat. Off. . |
| 0 461 630 | 12/1991 | European Pat. Off. . |
| 0 467 389 | 1/1992 | European Pat. Off. . |
| 0 481 732 | 4/1992 | European Pat. Off. . |
| 63-218632 | 9/1988 | Japan . |
| 2088314 | 6/1982 | United Kingdom . |
| 2209937 | 6/1989 | United Kingdom . |

OTHER PUBLICATIONS

Hutchinson et al., *Trends in Biotech* 5(4): 102 (1987).

*Primary Examiner*—Howard B. Schain
*Attorney, Agent, or Firm*—Foley & Lardner

[57] ABSTRACT

A sustained-release preparation which comprises a physiologically active peptide of general formula

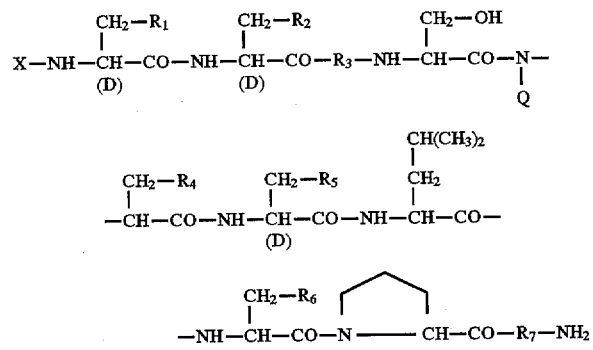

wherein X represents an acyl group;

$R_1$, $R_2$ and $R_4$ each represents an aromatic cyclic group;
$R_3$ represents a D-amino acid residue or a group of the formula

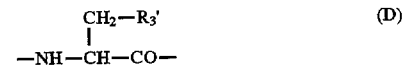

wherein $R_3'$ is a heterocyclic group;

$R_5$ represents a group of the formula $-(CH_2)_n-R_5'$ wherein n is 2 or 3, and $R_5'$ is an amino group which may optionally be substituted, an aromatic cyclic group or an O-glycosyl group;

$R_6$ represents a group of the formula $-(CH_2)_n-R_6'$ wherein n is 2 or 3, and $R_6'$ is an amino group which may optionally be substituted;

$R_7$ represents a D-amino acid residue or an azaglycyl residue; and

Q represents hydrogen or a lower alkyl group, or a salt thereof and a biodegradable polymer having a terminal carboxyl group.

The sustained-release preparation shows a constant release of the peptide over a long time and is substantially free from an initial burst.

6 Claims, No Drawings

SUSTAINED-RELEASE PREPARATION

This application is a divisional of application Ser. No. 08/162,698 filed Dec. 7, 1993, now U.S. Pat. No. 5,480,868.

The present invention relates to a sustained-release preparation containing a physiologically active peptide and to a method of producing the same.

BACKGROUND OF THE INVENTION

The prior art includes, as disclosed in EP-A-481,732, a sustained-release preparation comprising a drug, a polylactic acid and a glycolic acid-hydroxycarboxylic acid [HOCH$(C_{2-8}$ alkyl)COOH] copolymer. The disclosed process comprises preparing a W/O emulsion consisting of an internal water phase comprising an aqueous solution of a physiologically active peptide and an external oil phase comprising a solution of a biodegradable polymer in an organic solvent, adding said W/O emulsion to water or an aqueous medium and processing the resulting W/O/W emulsion into sustained-release microcapsules (drying-in-water method).

EP-A-52510 describes a microcapsule comprising a hormonally active polypeptide, a biodegradable polymer and a polymer hydrolysis control agent. The disclosed process for its production is a coacervation process which comprises adding a coacervation agent to a W/O emulsion consisting of an aqueous solution of the polypeptide as the internal water phase and a halogenated organic solvent as the oil phase to provide microcapsules.

GB-A-2209937 describes a pharmaceutical composition comprising a polylactide, a polyglycolide, a lactic acid-glycolic acid copolymer or a mixture of these polymers and a water-insoluble peptide. Also disclosed is a production process which comprises dispersing a salt of the water-insoluble peptide in a solution of said polylactide, polyglycolide, a lactic acid-glycolic acid copolymer or a mixture of these polymers, removing the solvent by evaporation and molding the resulting mixture into solid particles.

EP-A-58481 describes a process for producing a pharmaceutical composition comprising a polylactide and an acid-stable polypeptide which, for instance, comprises dissolving tetragastrin hydrochloride and a polylactide in aqueous dioxane, casting the solution into a film and evaporating the solvent.

EP-A-0467389 teaches a technology for providing a drug delivery system for proteins and polypeptides by the polymer precipitation technique or the microsphere technique. However, this literature contains no specific disclosure about a system containing an LH-RH derivative.

The luteinizing hormone-releasing hormone, known as LH-RH (or GnRH), is secreted from the hypothalamus and binds to receptors on the pituitary gland. The LH (luteinizing hormone) and FSH (follicle stimulating hormone), which are released thereon, act on the gonad to synthesize steroid hormones. As derivatives of LH-RH, the existence of both agonistic and antagonistic peptides is known. When a highly agonistic peptide is repeatedly administered, the available receptors are reduced in number so that the formation of gonad-derived steroidal hormones is suppressed. Therefore, LH-RH derivatives are expected to be of value as therapeutic agents for hormone-dependent diseases such as prostate cancer, benign prostatomegaly, endometriosis, hysteromyoma, metrofibroma, precocious puberty, mammary cancer, etc. or as contraceptives. Particularly, the problem of histamine-releasing activity was pointed out for LH-RH antagonists of the so-called first and second generations (The Pharmaceuticals Monthly 32, 1599–1605, 1990) but a number of compounds have since been synthesized and recently LH-RH-antagonizing peptides having no appreciable histamine-releasing activity have been developed (cf. U.S. Pat. No. 5,110,904, for instance). In order for any such LH-RH antagonizing peptide to manifest its pharmacological effect, there is a need for a controlled release system so that the competitive inhibition of endogenous LH-RH may be persistent. Moreover, because of histamine-releasing activity which may be low but is not non-existent in such peptides, a demand exists for a sustained-release preparation with an inhibited initial burst immediately following administration.

Particularly, in the case of a sustained-release (e.g. 1–3 months) preparation, it is important to insure a more positive and constant release of the peptide in order that the desired efficacy may be attained with greater certainty and safety.

At the same time, there is a long-felt need for a method of producing a sustained-release preparation having a high peptide trap rate for a physiologically active peptide, particularly LH-RH-antagonizing peptides.

SUMMARY OF THE INVENTION

According to the present invention, there is provided:

1) A sustained-release preparation which comprises a physiologically active peptide of the general formula $$X-NH-\underset{(D)}{CH}(CH_2-R_1)-CO-NH-\underset{(D)}{CH}(CH_2-R_2)-CO-R_3-NH-CH(CH_2-OH)-CO-N(CH_2-R_4)-CH-CO-$$
$$| \atop Q$$

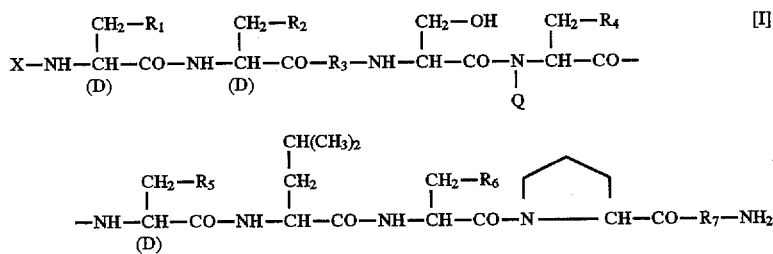

$$-NH-\underset{(D)}{CH}(CH_2-R_5)-CO-NH-CH(CH_2-CH(CH_3)_2)-CO-NH-CH(CH_2-R_6)-CO-N\overset{\frown}{\underline{\quad\quad}}CH-CO-R_7-NH_2$$

wherein X represents an acyl group;
R$_1$, R$_2$ and R$_4$ each represents an aromatic cyclic group;
R$_3$ represents a D-amino acid residue or a group of the formula

$$-NH-\underset{(D)}{CH}(CH_2-R_3')-CO-$$

wherein R$_3$' is a heterocyclic group;
R$_5$ represents a group of the formula —(CH$_2$)$_n$—R$_5$' wherein n is 2 or 3, and R$_5$' is an amino group which may optionally be substituted, an aromatic cyclic group or an O-glycosyl group;

$R_6$ represents a group of the formula $-(CH_2)_n-R_6'$ wherein n is 2 or 3, and $R_6'$ is an amino group which may optionally be substituted;

$R_7$ represents a D-amino acid residue or an azaglycyl residue; and

Q represents hydrogen or a lower alkyl group or a salt thereof and a biodegradable polymer having a terminal carboxyl group, 2) The sustained-release preparation according to the above paragraph 1, wherein X is a $C_{2-7}$ alkanoyl group which may optionally be substituted by a 5- or 6-membered heterocyclic carboxamido group, 3) The sustained-release preparation according to the above paragraph 2, wherein X is a $C_{2-4}$ alkanoyl group which may optionally be substituted by a tetrahydrofurylcarboxamide group, 4) The sustained-release preparation according to the above paragraph 1, wherein X is acetyl, 5) The sustained-release preparation according to the above paragraph 1, wherein the biodegradable polymer is a mixture of (A) a copolymer of glycolic acid and a hydroxycarboxylic acid of the general formula $$\underset{\text{HOCHCOOH}}{\overset{R}{|}} \quad [\text{II}]$$

wherein R represents an alkyl group of 2 to 8 carbon atoms and (B) a polylactic acid, 6) The sustained-release preparation according to the above paragraph 1, wherein X is acetyl, and the biodegradable polymer is a mixture of (A) a copolymer of glycolic acid and a hydroxycarboxylic acid of the general formula [II] and (B) a polylactic acid, 7) The sustained-release preparation according to the above paragraph 5, wherein the copolymer has a weight average molecular weight of about 2,000 to 50,000, as determined by GPC, 8) The sustained-release preparation according to the above paragraph 5, wherein the copolymer has a dispersion value of about 1.2 to 4.0, 9) The sustained-release preparation according to the above paragraph 5, wherein the polylactic acid has a weight average molecular weight of about 1,500 to 30,000 as determined by GPC, 10) The sustained-release preparation according to the above paragraph 5, wherein the polylactic acid has a dispersion value of about 1.2 to 4.0, 11) The sustained-release preparation according to the above paragraph 1, wherein the biodegradable polymer is a copolymer of lactic acid and glycolic acid, 12) The sustained-release preparation according to the above paragraph 11, wherein the copolymer has a weight average molecular weight of about 5,000 to 25,000, as determined by GPC, 13) The sustained-release preparation according to the above paragraph 11, wherein the copolymer has a dispersion value of about 1.2 to 4.0, 14) The sustained-release preparation according to the above paragraph 1, wherein the proportion of the physiologically active peptide ranges from about 0.01 to 50% (w/w) based on the biodegradable polymer, 15) The sustained-release preparation according to the above paragraph 1, wherein the physiologically active peptide is a LH-RH antagonist, 16) The sustained-release preparation according to the above paragraph 1, wherein the physiologically active peptide is

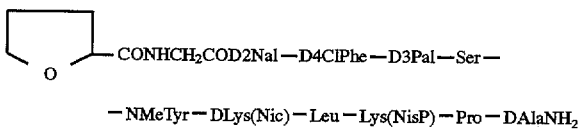

—NMeTyr—DLys(Nic)—Leu—Lys(NisP)—Pro—DAlaNH₂ or its acetate,

17) The sustained-release preparation according to the above paragraph 1, wherein the physiologically active peptide is NAcD2Nal-D4ClPhe-D3Pal-Ser-NMeTyr-DLys(Nic)-Leu-Lys(Nisp)-Pro-DAlaNH₂ or its acetate, 18) The sustained-release preparation according to the above paragraph 1, wherein the physiologically active peptide is NAcD2Nal-D4ClPhe-D3Pal-Ser-Tyr-DhArg(Et₂)-Leu-hArg(Et₂)-Pro-DAlaNH₂ or its acetate, 19) A method of producing a sustained-release preparation which comprises dissolving a physiologically active peptide of the general formula [I] or a salt thereof and a biodegradable polymer having a terminal carboxyl group in a solvent which is substantially immiscible with water and then removing said solvent, 20) The method according to the above paragraph 19, wherein the biodegradable polymer is a mixture of (A) a copolymer of glycolic acid and a hydroxycarboxylic acid of the general formula [II] and (B) a polylactic acid, 21) The method according to the above paragraph 19, wherein X is acetyl, and the biodegradable polymer is a mixture of (A) a copolymer of glycolic acid and a hydroxycarboxylic acid of the general formula [II] and (B) a polylactic acid, 22) The method according to the above paragraph 19, wherein the biodegradable polymer is a copolymer of lactic acid and glycolic acid, 23) A method according to the above paragraph 19, which comprises dissolving the biodegradable polymer and the physiologically active peptide in a solvent which is substantially immiscible with water and adding the resulting solution to an aqueous medium to provide an O/W emulsion, 24) A method of producing a sustained-release preparation which comprises dissolving a biodegradable polymer comprising a mixture of (A) a copolymer of glycolic acid and a hydroxycarboxylic acid of the general formula

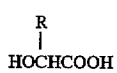

wherein R represents an alkyl group of 2 to 8 carbon atoms and (B) a polylactic acid and a substantially water-insoluble physiologically active peptide or a salt thereof in a solvent which is substantially immiscible with water and then removing said solvent, and 25) A method according to the above paragraph 24, which further comprises after dissolving the biodegradable polymer and the substantially water-insoluble peptide or salt thereof in the solvent adding the resulting solution to an aqueous medium to provide an O/W emulsion.

DETAILED DESCRIPTION OF THE INVENTION

The abbreviations used in this specification have the following meanings.

NAcD2Nal: N-Acetyl-D-3-(2-naphtyl)alanyl
D4ClPhe: D-3-(4-Chlorophenyl)alanyl
D3Pal: D-3-(3-Pyridyl)alanyl
NMeTyr: N-Methylthyrosyl
DLys(Nic): D-(Ipsilon-N-nicotinoyl)lysyl
Lys(Nisp): (Ipsilon-N-isopropyl)lysyl
DLys(AzaglyNic): D-[1-Aza-(N-nicotinoyl)glycyl]lysyl
DLys(AzaglyFur): D-[1-Aza-(N-2-furoyl)glycyl]lysyl Where any other amino acids are expressed by abbreviations, the abbreviations recommended by IUPAC-IUB Commission on Biochemical Nomenclature (European Journal of Biochemistry 138, 9–37, 1984) or the abbreviations in common usage in the art are used. Where optical isomers exist for any compound, the L-isomer is meant unless otherwise indicated.

In the present invention, the peptide [I] shows LH-RH antagonistic activity and is effective for the treatment of hormone-dependent diseases such as prostatic cancer, prostatomegaly, endometriosis, hysteromyoma, metrofibroma, precocious puberty, mammary cancer, etc. or for contraception.

Referring to general formula [I], the acyl group X is preferably an acyl group derived from carboxylic acid. Examples of the acyl group include a $C_{2-7}$ alkanoyl, $C_{7-15}$ cycloalkenoyl (e.g., cyclohexenoyl), $C_{1-6}$ alkylcarbamoyl (e.g., ethyl carbamoyl), 5- or 6-membered heterocyclic carbonyl (e.g. piperidinocarbonyl) and carbamoyl group which may optionally be substituted. The acyl group is preferably a $C_{2-7}$ alkanoyl group (e.g., acetyl, propionyl, butyryl, isobutyryl, pentanoyl, hexanoyl or heptanoyl) which may optionally be substituted, more preferably $C_{2-4}$ alkanoyl group (e.g., acetyl, propionyl, butyryl, isobutyryl) which may optionally be substituted. The substituents are for example $C_{1-6}$ alkylamino group (e.g., methylamino, ethylamino, diethylamino, propylamino), $C_{1-3}$ alkanoyl amino group (e.g., formylamino, acetylamino, propionylamino), $C_{7-15}$ cycloalkenoyl amino group (e.g., cyclohexenoylamino), $C_{7-15}$ arylcarbonyl-amino group (e.g., benzoylamino), 5- or 6-membered heterocyclic carboxamido group (e.g., tetrahydrofurylcarboxamide, pyridylcarboxamido, furylcarboxamido), hydroxyl group, carbamoyl group, formyl group, carboxyl group, 5- or 6-membered heterocyclic group (e.g., pyridyl, morpholino). The substituents are preferably 5- or 6-membered heterocyclic carboxamido group (e.g., tetrahydrofurylcarboxamido, pyridylcarboxamido, furylcarboxamido).

X is preferably a $C_{2-7}$ alkanoyl group which may optionally be substituted by a 5- or 6-membered heterocyclic carboxamido group.

X is more preferably a $C_{2-4}$ alkanoyl group which may optionally be substituted by a tetrahydrofuryl carboxamido group.

Specific examples of X are acetyl,

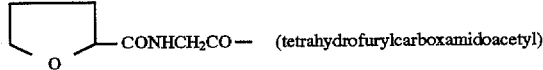 (tetrahydrofurylcarboxamidoacetyl)

and so on.

The aromatic cyclic group $R_1$, $R_2$ or $R_4$ may for example be an aromatic cyclic group of 6 to 12 carbon atoms. Examples of the aromatic cyclic group are phenyl, naphthyl, anthryl and so on. Preferred are aromatic cyclic groups of 6 to 10 carbon atoms, such as phenyl and naphthyl. These aromatic cyclic groups may each have 1 to 5, preferably 1 to 3, suitable substituents in appropriate positions on the ring. Such substituents include hydroxyl, halogen, aminotriazolyl-substituted amino, alkoxy and so on. Preferred are hydroxy, halogen and aminotriazolyl-substituted amino.

The halogens mentioned above include fluorine, chlorine, bromine and iodine.

The aminotriazolyl moiety of said aminotriazolyl-substituted amino includes, among others, 3-amino-1H-1,2,4-triazol-5-yl, 5-amino-1H-1,3,4-triazol-2-yl, 5-amino-1H-1,2,4-triazol-3-yl, 3-amino-2H-1,2,4-triazol-5-yl, 4-amino-1H-1,2,3-triazol-5-yl, 4-amino-2H-1,2,3-triazol-5-yl and so on.

The alkoxy group is preferably an alkoxy group of 1 to 6 carbon atoms (e.g. methoxy, ethoxy, propoxy, isopropoxy, butoxy, isobutoxy, etc.).

More preferably, $R_1$ is naphthyl or halophenyl. More preferably, $R_2$ is halophenyl. More preferably, $R_4$ is hydroxyphenyl or aminotriazolylamino-substituted phenyl.

The D-amino acid residue $R_3$ is preferably an α-D-amino acid residue of 3 to 12 carbon atoms. Examples of the amino acid are leucine, isoleucine, norleucine, valine, norvaline, 2-aminobutyric acid, phenylalanine, serine, threonine, methionine, alanine, tryptophan and aminoisobutyric acid. These amino acids may have suitable protective groups (the protective groups used conventionally in the art, such as t-butyl, t-butoxy, t-butoxycarbonyl, etc.).

The heterocyclic group $R_3'$ includes 5- or 6-membered heterocyclic groups each containing 1 to 2 nitrogen or sulfur atoms as hetero-atoms, which may optionally be fused to a benzene ring. Specifically, thienyl, pyrrolyl, thiazolyl, isothiazolyl, imidazolyl, pyrazolyl, pyridyl, 3-pyridyl, pyridazinyl, pyrimidinyl, pyrazinyl, 3-benzo[b]thienyl, 3-benzo[b]-3-thienyl, indolyl, 2-indolyl, isoindolyl, 1H-indazolyl, benzoimidazolyl, benzothiazolyl, quinolyl, isoquinolyl, etc. may be mentioned. The particularly preferred species of $R_3'$ is pyridyl or 3-benzo[b]thienyl.

The aromatic cyclic group $R_5$ may be the same as the aromatic cyclic group $R_1$, $R_2$ or $R_4$. The aromatic cyclic group may have 1 to 5, preferably 1 to 3, suitable substituents in appropriate positions on the ring. The substituents may also be the same as the substituents mentioned for $R_1$, $R_2$ or $R_4$. The particularly preferred substituent is aminotriazolyl-substituted amino.

The glycosyl group for O-glycosyl $R_5$ is preferably a hexose or a derivative thereof. The hexose includes D-glucose, D-fructose, D-mannose, D-galactose, L-galactose and so on. As said derivative, deoxy sugars (L- and D-fucose, D-quinovose, L-rhamnose, etc.) and amino sugars (D-glucosamine, D-galactosamine, etc.) can be mentioned. More preferred are deoxy sugars (L- and D-fucose, D-quinovose, L-rhamnose, etc.). Still more preferred is L-rhamnose.

The substituent on the amino group which may optionally be substituted, $R_5'$, includes, among others, acyl, carbamoyl, carbazoyl which may be substituted by acyl or amidino which may be mono- or di-substituted by alkyl.

The above-mentioned acyl and the acyl for the above-mentioned carbazoyl which may be substituted by acyl include nicotinoyl, furoyl, thenoyl and so on.

The alkyl moiety of the mono- or di-alkylamidino mentioned above includes straight-chain or branched alkyl groups of 1 to 4 carbon atoms, thus including methyl, ethyl, propyl, isopropyl, butyl, isobutyl, sec-butyl and tert-butyl and so on. The preferred alkyl moiety is methyl or ethyl.

The substituent for the amino group which may optionally be substituted, $R_6'$, includes alkyl and amidino which may be mono- or di-substituted by alkyl.

The above-mentioned alkyl and the alkyl of the mono- or dialkylamidino mentioned above include those alkyl groups mentioned for $R_5'$.

The D-amino acid residue $R_7$ is preferably a D-amino acid residue of 3 to 9 carbon atoms, such as D-alanyl, D-leucyl, D-valyl, D-isoleucyl, D-phenylalanyl and so on. More preferred are D-amino acid residues of 3 to 6 carbon atoms, such as D-alanyl, D-valyl and so on. The more preferred species of $R_7$ is D-alanyl.

The lower alkyl group Q may be the alkyl group defined for $R_5'$. The most preferred species of Q is methyl.

Specific examples of $R_1$ are

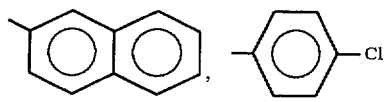

and so on.

Specific examples of $R_2$ are

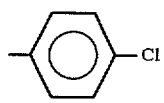

and so on.

Specific examples of $R_3$ are

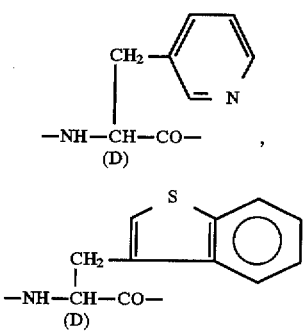

and so on.

Specific examples of $R_4$ are

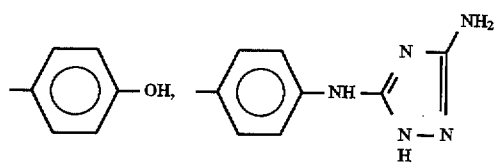

and so on.

Specific examples of $R_5$ are

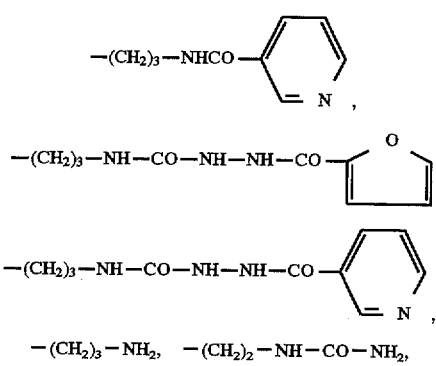

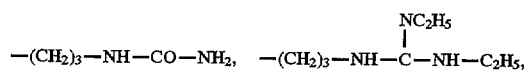

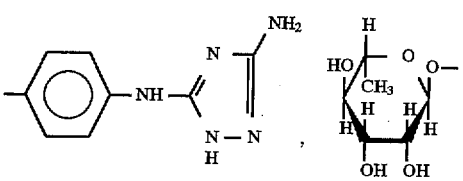

and so on.

Specific examples of $R_6$ are

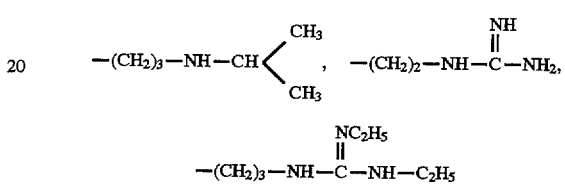

and so on.

Specific examples of $R_7$ are

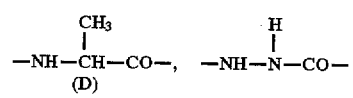

and so on.

When the peptide [I] has one or more asymmetric carbon atom(s), there are two or more stereoisomers. Any of such steroisomers as well as a mixture thereof is within the scope of the present invention.

The peptide of general formula [I] is produced by the per se known processes. Typical specific processes are described in U.S. Pat. No. 5,110,904.

The peptide [I] can be used in the form of a salt, preferably a pharmacologically acceptable salt. Where the peptide has basic groups such as amino, the salt includes salts with inorganic acids (e.g. hydrochloric acid, sulfuric acid, nitric acid, etc.) or organic acids (e.g. carbonic acid, hydrogen carbonic acid, succinic acid, acetic acid, propionic acid, trifluoroacetic acid, etc.). Where the peptide has acidic groups such as carboxyl, salts with inorganic bases (e.g. alkali metals such as sodium, potassium, etc. and alkaline earth metals such as calcium, magnesium, etc.) or organic bases (e.g. organic amines such as triethylamine and basic amino acids such as arginine). The peptide [I] may be in the form of a metal complex compound (e.g. copper complex, zinc complex, etc.). The preferred salts of peptide [I] are salts with organic acids (e.g. carbonic acid, hydrogen carbonic acid, succinic acid, acetic acid, propionic acid, trifluoroacetic acid, etc.). The most preferred is the acetate.

Particularly preferred species of peptide [I] or salt are as follows.

(1) NAcD2Nal-D4ClPhe-D3Pal-Ser-NMeTyr-DLys(Nic)-Leu-Lys(Nisp)-Pro-DAlaNH$_2$ or its acetate (2) NAcD2Nal-D4ClPhe-D3Pal-Ser-NMeTyr-DLys(AzaglyNic)-Leu-Lys(Nisp)-Pro-DAlaNH$_2$ or its acetate (3) NAcD2Nal-D4ClPhe-D3Pal-Ser-NMeTyr-DLys(AzaglyFur)-Leu-Lys(Nisp)-Pro-DAlaNH$_2$ or its acetate (4) 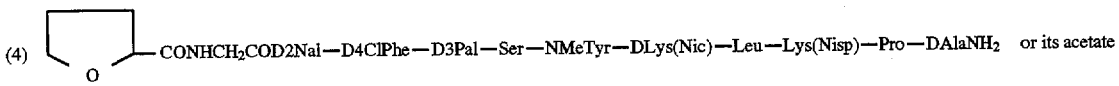CONHCH₂COD2Nal—D4ClPhe—D3Pal—Ser—NMeTyr—DLys(Nic)—Leu—Lys(Nisp)—Pro—DAlaNH₂ or its acetate (5) NAcD2Nal-D4ClPhe-D3Pal-Ser-Tyr-DhArg(Et₂)-Leu-hArg(Et₂)-Pro-DAlaNH₂ or its acetate In the sustained-release preparation, the proportion of the peptide [I] may vary with the type of peptide, the expected pharmacological effect and duration of effect, among other factors, and may range from about 0.01 to about 50% (w/w) based on the biodegradable polymer. The preferred range is about 0.1 to about 40% (w/w) and a more preferred range is about 1 to about 30% (w/w).

The biodegradable polymer having a terminal carboxyl group is now described.

A biodegradable polymer, about 1 to 3 g, was dissolved in a mixture of acetone (25 ml) and methanol (5 ml) and using phenolphthalein as the indicator, the carboxyl groups in the solution were quickly titrated with 0.05N alcoholic potassium hydroxide solution under stirring at room temperature (20° C). The number average molecular weight by end-group determination was then calculated by means of the following equation.

Number average molecular weight by end-group determination=20000×A/B where

A is the mass of biodegradable polymer (g)

B is the amount of 0.05N alcoholic potassium hydroxide solution (ml) added to react the titration end-point.

The result of the above calculation is referred to as the number average molecular weight by end-group determination.

By way of illustration, taking a polymer having a terminal carboxyl group as synthesized from one or more α-hydroxy acids by the non-catalytic dehydrative polycondensation process as an example, the number average molecular weight by end-group determination is approximately equal to the number average molecular weight found by GPC. In contrast, in the case of a polymer substantially not containing free terminal carboxyl groups as synthesized from a cyclic dimer by the ring-opening polymerization process and using catalysts, the number average molecular weight by end-group determination is by far greater than the number average molecular weight by GPC determination. By this difference, a polymer having a terminal carboxyl group can be clearly discriminated from a polymer having no terminal carboxyl group. Thus, the term 'biodegradable polymer having a terminal carboxyl group' is used herein to mean a biodegradable polymer showing a substantial agreement between the number average molecular weight by GPC determination and the number average molecular weight by end-group determination.

Whereas the number average molecular weight by end-group determination is an absolute value, the number average molecular weight by GPC determination is a relative value which varies according to analytical and procedural conditions (such as types of mobile phase and column, reference substance, selected slice width, selected baseline, etc.). Therefore, the two values cannot be numerically correlated by generalization. However, the term 'substantial agreement' between the number average molecular weight by GPC determination and the number average molecular weight by end-group determination means that the number average molecular weight found by end-group determination is about 0.4 to 2 times, more preferably about 0.5 to 2 times, most preferably about 0.8 to 1.5 times, the number average molecular weight by GPC determination. The term 'by far greater' as used above means that the number average molecular weight by end-group determination is about twice or greater than the number average molecular weight by GPC determination.

The preferred polymer for the purpose of the present invention is a polymer showing a substantial agreement between the number average molecular weight by GPC determination and the number average molecular weight by end-group determination.

As specific examples of the biodegradable polymer having a terminal carboxyl group can be mentioned polymers and copolymers, as well as mixtures thereof, which are synthesized from one or more species of α-hydroxy acids (e.g. glycolic acid, lactic acid, hydroxybutyric acid, etc.), hydroxydicarboxylic acids (e.g. malic acid etc.), hydroxytricarboxylic acids (e.g. citric acid etc.), etc. by the non-catalytic dehydrative polycondensation reaction, poly-α-cyanoacrylic esters, polyamino acids (e.g. poly-γ-benzyl-L-glutamic acid etc.), maleic anhydride copolymers (e.g. styrene-maleic acid copolymer etc.) and so on.

The mode of polymerization may be random, block or graft. Where any of the above-mentioned α-hydroxy acids, hydroxydicarboxylic acids and hydroxytricarboxylic acids has an optical activity center within the molecule, any of the D-, L- and DL-forms can be employed.

The biodegradable polymer having a terminal carboxyl group is preferably a biodegradable polymer comprising a mixture of (A) a copolymer of glycolic acid and a hydroxycarboxylic acid of the general formula

wherein R represents an alkyl group of 2 to 8 carbon atoms and (B) a polylactic acid, or a lactic acid-glycolic acid copolymer.

Referring to the general formula [II], the straight-chain or branched alkyl group of 2 to 8 carbon atoms, as represented by R, includes, inter alia, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl. Preferred, among them, are straight-chain or branched alkyls of 2 to 5 carbon atoms. Specifically, ethyl, propyl, isopropyl, butyl and isobutyl are preferred. R is most preferably ethyl.

The hydroxycarboxylic acid of the general formula [II] includes, inter alia, 2-hydroxybutyric acid, 2-hydroxyvaleric acid, 2-hydroxy-3-methylbutyric acid, 2-hydroxycaproic acid, 2-hydroxyisocaproic acid and 2-hydroxycapric acid. Preferred are 2-hydroxybutyric acid, 2-hydroxyvaleric acid, 2-hydroxy-3-methylbutyric acid and 2-hydroxycaproic acid. The hydroxycarboxylic acid of the general formula [II] is most preferably 2-hydroxybutyric acid. While these hydroxycarboxylic acids may be any of the D-, L- and D,L-compounds, the D-/L-ratio (mol %) is preferably in the range of about 75/25 through about 25/75. The more preferred embodiment is a hydroxycarboxylic acid with a D-/L-ratio (mol %) within the range of about 60/40 through about 40/60. The most preferred is a hydroxycarboxylic acid with a D-/L-ratio (mol %) within the range of about 55/45 through about 45/55.

Referring to the copolymer of glycolic acid and said hydroxycarboxylic acid of the general formula [II] (hereinafter referred to as glycolic acid copolymer), the mode of copolymerization may be random, block or graft. Preferred are random copolymers.

The hydroxycarboxylic acids of the general formula [II] can be used alone or in combination.

The preferred proportions of glycolic acid and hydroxycarboxylic acid [II] in said glycolic acid copolymer (A) are about 10 to about 75 mole % of glycolic acid and the balance of hydroxycarboxylic acid. More desirably, the copolymer consists of about 20 to about 75 mole % of glycolic acid and the balance of hydroxycarboxylic acid. Most desirably, the copolymer consists of about 40 to about 70 mole % of glycolic acid and the balance of hydroxycarboxylic acid. The weight average molecular weight of said glycolic acid copolymer may range from about 2,000 to about 50,000. The preferred range is about 3,000 to about 40,000. The more preferred range is about 8,000 to about 30000. The dispersion value (weight average molecular weight/number average molecular weight) is preferably in the range of about 1.2 to about 4.0. Particularly preferred are copolymers with dispersion values in the range of about 1.5 to about 3.5.

The glycolic acid copolymer (A) can be synthesized by the known technology, for example by the process described in Japanese laid-open patent application 28521/1986 specification.

Polylactic acid for use in the present invention may be whichever of L- and D-compounds and any mixture thereof. Preferred is a species with a D-/L-ratio (mole %) in the range of about 75/25 through about 20/80. The more preferred D-/L-ratio (mole %) of polylactic acid is about 60/40 through about 25/75. The most advantageous D/L-ratio (mole %) of polylactic acid is about 55/45 through about 25/75. The weight average molecular weight of polylactic acid is preferably in the range of about 1,500 to about 30,000, more preferably about 2,000 to about 20,000 and still more preferably about 3,000 to about 15,000. The dispersion value of polylactic acid is preferably about 1.2 to about 4.0 and more desirably about 1.5 to about 3.5.

Polylactic acid can be synthesized by two known alternative processes, namely a process involving a ring-opening polymerization of lactide which is a dimer of lactic acid and a process involving a dehydrative polycondensation of lactic acid. For the production of a polylactic acid of comparatively low molecular weight for use in the present invention, the process involving a direct dehydrative polycondensation of lactic acid is preferred. This process is described in, for example, Japanese laid-open patent application 28521/1986.

In the pharmaceutical base for use in the present invention, the glycolic acid copolymer (A) and polylactic acid (B) are used in an (A)/(B) ratio (by weight) of about 10/90 through about 90/10. The preferred blend ratio is about 20/80 through about 80/20. The most desirable ratio is about 30/70 through about 70/30. If the proportion of either (A) or (B) is too large, the final preparation will show a drug release pattern not much different from the pattern obtained when (A) or (B) alone is used, that is to say the linear release pattern in a late stage of release which is obtainable with the mixed base cannot be obtained. The degradation and elimination rates of glycolic acid copolymer and polylactic acid vary considerably with their molecular weights and composition but generally speaking, since the decomposition and elimination rates of glycolic acid copolymer are relatively higher, the period of release can be prolonged by increasing the molecular weight of polylactic acid or reducing the blend ratio (A)/(B). Conversely, the duration of release may be shortened by reducing the molecular weight of polylactic acid or increasing the (A)/(B) blend ratio. Furthermore, the duration of release can be adjusted by changing the species or relative amount of hydroxycarboxylic acid of general formula [II].

When a copolymer of lactic acid and glycolic acid is used as the biodegradable polymer, its polymerization ratio (lactic acid/glycolic acid) (mole %) is preferably about 100/0 to about 40/60. The more preferred ratio is about 90/10 to about 50/50.

The weight average molecular weight of said copolymer is preferably about 5,000 to about 25,000. The more preferred range is about 7,000 to about 20,000.

The degree of dispersion (weight average molecular weight/number average molecular weight) of said copolymer is preferably about 1.2 to about 4.0. The more preferred range is about 1.5 to about 3.5.

The above-mentioned copolymer of lactic acid and glycolic acid can be synthesized by the known technology, for example by the process described in Japanese laid-open patent application 28521/1986.

The decomposition and disappearance rate of a copolymer of lactic acid and glycolic acid varies greatly with the composition and molecular weight but generally speaking, the smaller the glycolic acid fraction, the lower is the decomposition and disappearance rate. Therefore, the duration of drug release can be prolonged by reducing the glycolic acid fraction or increasing the molecular weight. Conversely, the duration of release can be diminished by increasing the glycolic acid fraction or reducing the molecular weight. To provide a long-term (e.g. 1~4 months) sustained-release preparation, it is preferable to use a copolymer of lactic acid and glycolic acid with a polymerization ratio within the above-mentioned range and a weight average molecular weight within the above-mentioned range. With a copolymer of lactic acid and glycolic acid having a higher decomposition rate than that within the above ranges for polymerization ratio and weight average molecular weight, it is difficult to control the initial burst. On the contrary, with a copolymer of lactic acid and glycolic acid showing a lower decomposition rate than that within said ranges for polymerization ratio and weight average molecular weight, periods in which the drug will not be released in an effective amount tend to occur.

In this specification, the weight average molecular weight and the degree of dispersion mean the molecular weight in terms of polystyrene as determined by gel permeation chromatography (GPC) using 9 polystyrenes with the weight average molecular weights of 120,000, 52,000, 22,000, 9,200, 5,050, 2950, 1,050, 580 and 162 as references and the dispersion value calculated using the same molecular weight, respectively. The above determination was carried out using GPC Column KF804 L×2 (Showa Denko), RI Monitor L-3300 (Hitachi) and, as the mobile phase, chloroform.

The sustained-release preparation of the present invention is produced by dissolving the peptide [I] and a biodegradable polymer having a terminal carboxyl group in a solvent which is substantially immiscible with water and then removing said solvent.

The solvent which is substantially immiscible with water is a solvent which is not only substantially immiscible with water and capable of dissolving the biodegradable polymer but one which renders the resultant polymer solution capable of dissolving the peptide [I]. Preferably, it is a solvent with a solubility in water of not more than 3% (w/w) at atmospheric temperature (20° C.) The boiling point of such solvent is preferably not higher than 120° C. The solvent, thus, includes halogenated hydrocarbons (e.g. dichloromethane, chloroform, chloroethane, trichloroethane, carbon tetrachloride, etc.), alkyl ethers of 3 or more carbon atoms (e.g. isopropyl ether etc.), fatty acid alkyl (of 4 or more carbon atoms) esters (e.g. butyl acetate etc.), aromatic hydrocarbons (e.g. benzene, toluene, xylene, etc.) and so on. These solvents can be used in a suitable combination of 2 or more species. The more preferred solvents are halogenated hydrocarbons (e.g. dichloromethane, chloroform, chloroethane, trichloroethane, carbon tetrachloride, etc.). The most preferred is dichloromethane.

Removal of the solvent can be effected by the per se known procedures. For example, the method comprising evaporating the solvent at atmospheric pressure or under gradual decompression with constant stirring by means of a propeller mixer or a magnetic stirrer or the method comprising evaporating the solvent under controlled vacuum in a rotary evaporator can be employed.

Referring to the method of the invention for the production of the sustained-release preparation, dissolving the peptide [I] and a biodegradable polymer with a terminal carboxyl group means achieving a condition such that the resultant solution shows no visually observable residue of undissolved peptide at ordinary temperature (20° C.). In this ternary system consisting of the peptide [I], biodegradable polymer and solvent, the amount of peptide which can be dissolved depends on the number of a terminal carboxyl groups per unit weight of the biodegradable polymer. In case the peptide and the terminal carboxyl group interact in the ratio of 1 to 1, the same molar amount of the peptide as that of the terminal carboxyl group can be dissolved in theory. Therefore, generalization is difficult according to the combination of the solvent and the molecular weight of the peptide and the biodegradable polymer. However, in producing sustained-release preparations, the peptide may be dissolved in the range of about 0.1 to about 100% (w/w), preferably about 1 to about 70% (w/w), most preferably about 2 to about 50% (w/w), with respect to the biodegradable polymer which is dissolved in the solvent.

The present invention is further related to a method of producing a sustained-release preparation which comprises dissolving a biodegradable polymer comprising a mixture of (A) a copolymer of glycolic acid and a hydroxycarboxylic acid of the general formula

wherein R represents an alkyl group of 2 to 8 carbon atoms and (B) a polylactic acid and a substantially water-insoluble physiologically active peptide or a salt thereof in a solvent which is substantially immiscible with water and then removing said solvent.

The substantially water-insoluble physiologically active peptide is not limited and includes naturally-occurring, synthetic and semi-synthetic peptides. Preferred are physiologically active peptides containing one or more aromatic groups (e.g. groups derived from benzene, naphthalene, phenanthrene, anthracene, pyridine, pyrole, indole, etc.) in side chains thereof. More preferred physiologically active peptides are those having 2 or more aromatic groups in side chains thereof. Particularly preferred physiologically active peptides are those having 3 or more aromatic groups in side chains thereof. These aromatic groups may be further substituted.

The substantially water-insoluble physiologically active peptide for use in the present invention is preferably a peptide showing a solubility of not more than 1% in water, consisting of two or more amino acids and having a molecular weight of about 200 to 30000. The molecular weight range is more preferably about 300 to 20000 and still more preferably about 500 to 10000.

As examples of said physiologically active peptide may be mentioned luteinizing hormone releasing hormone (LH-RH) antagonists (cf. U.S. Pat. No. 4,086,219, 4,124,577, 4,253,997 and 4,317,815, etc.), insulin, somatostatin, somatostatin derivatives (cf. U.S. Pat. No. 4,087,390, 4,093,574, 4,100,117, 4,253,998, etc.), growth hormone, prolactin, adrenocorticotropic hormone (ACTH), melanocyte stimulating hormone (MSH), salts and derivatives of thyroid hormone releasing hormone (cf. JP Kokai S-50-121273 and S-52-116465), thyroid stimulating hormone (TSH), luteinizing hormone (LH), follicle stimulating hormone (FSH), vasopressin, vasopressin derivatives, oxytocin, calcitonin, gastrin, secretin, pancreozymin, cholecystokinin, angiotensin, human placental lactogen, human chorionic gonadotropin (HCG), enkepharin, enkephalin derivatives (cf. U.S. Pat. No. 4,277,394, EP-A No. 31,567), endorphin, kyotrphin, tuftsin, thymopoietin, thymosin, thymostimulin, thymic humoral factor (THF), facteur thymique sérique (FTS) and its derivatives (cf. U.S. Pat. No. 4,229,438), other thymic factors, tumor necrosis factor (TNF), colony stimulating factor (CSF), motilin, dynorphin, bombesin, neurotensin, cerulein, bradykinin, atrial natruretic factor, nerve growth factor, cell growth factor, neurotrophic factor, peptides having endothelin antagonistic activity (cf. EP-A No. 436189, No. 457195 and No. 496452, JP Kokai H-3-94692 and 03-130299) and fragments or derivatives of these physiologically active peptides.

Specific examples of the physiologically active peptide are physiologically active peptides and salts which are antagonists of luteinizing hormone releasing hormone (LH-RH) and useful for the treatment of hormone-dependent diseases such as prostatic cancer, prostatic hypertrophy, endometriosis, uterine myoma, precocious puberty, breast cancer, etc. and for contraception.

The physiologically active peptide for use in the present invention can be in the form of a salt, preferably a pharmacologically acceptable salt. Where said peptide has a basic group such as amino, the salt mentioned above may for example be the salt formed with an inorganic acid (e.g. hydrochloric acid, sulfuric acid, nitric acid, etc.) or an organic acid (e.g. carbonic acid, hydrogencarbonic acid, succinic acid, acetic acid, propionic acid, trifluoroacetic acid, etc.). Where the peptide has an acidic group such as carboxyl, the salt may for example be the salt formed with an inorganic base (e.g. alkali metals such as sodium, potassium, etc. and alkaline earth metals such as calcium, magnesium, etc.) or an organic base (e.g. organic amines such as triethylamine etc. and basic amino acids such as arginine etc.). The peptide may further be in the form of a metal complex compound (e.g. copper complex, zinc complex, etc.).

Specific examples of the physiologically active peptide or salt thereof are found in U.S. Pat. No. 5110904, Journal of Medicinal Chemistry 34, 2395–2402, 1991, Recent Results in Cancer Research 124, 113–136, 1992, and other literature.

Furthermore, the physiologically active peptides of general formula [I] and salts thereof can also be mentioned, among others.

Moreover, even when the physiologically active peptide is water-soluble, it can be converted to a derivative compound which is insoluble or converted to an insoluble salt with a water-insoluble acid (e.g. pamoic acid, tannic acid, stearic acid, palmitic acid, etc.) and used in the process of the invention.

The amount of said physiologically active peptide in the preparations of the present invention depends on the species of peptide, expected pharmacologic effect and desired duration of effect and so on. Generally, however, it is used in a proportion of about 0.001 to 50% (w/w), preferably about 0.01 to 40% (w/w), more preferably about 0.1 to 30% (w/w), relative to the biodegradable polymer base.

The solvent employed in the method is the same as described above.

Removal of the solvent can be carried out in the same manner as described above.

The preferred process for the production of the sustained-release preparation of the present invention is a microencapsulating process utilizing the drying-in-water technique or the phase separation technique, which is described below, or any process analogous thereto.

The process described below may be carried out with peptide [I] or with a substantially water-insoluble physiologically active peptide which includes peptide [I].

Thus, the peptide [I] is added to a solution of the biodegradable polymer in an organic solvent in the final weight ratio mentioned hereinbefore for such peptide to prepare an organic solvent solution containing the peptide [I] and biodegradable polymer. In this connection, the concentration of the biodegradable polymer in the organic solvent varies according to the molecular weight of the biodegradable polymer and the type of organic solvent but is generally selected from the range of about 0.01 to about 80% (w/w). The preferred range is about 0.1 to about 70% (w/w). The still more preferred range is about 1 to about 60% (w/w).

Then, this organic solvent solution containing the peptide [I] and biodegradable polymer (oil phase) is added to a water phase to prepare an O(oil phase)/W (water phase) emulsion. The solvent of the oil phase is then evaporated off to provide microcapsules. The volume of the water phase for this procedure is generally selected from the range of about 1 to about 10000 times the volume of the oil phase. The preferred range is about 2 to about 5000 times and the still more preferred range is about 5 to about 2000 times.

An emulsifier may be added to the above water phase. The emulsifier may generally be any substance that contributes to the formation of a stable O/W emulsion. Thus, there can be mentioned anionic surfactants (sodium oleate, sodium stearate, sodium lauryl sulfate, etc.), nonionic surfactants (polyoxyethylene-sorbitan fatty acid esters [Tween 80 and Tween 60, Atlas Powder], polyoxyethylene-castor oil derivatives [HCO-60 and HCO-50, Nikko Chemicals], etc.), polyvinylpyrrolidone, polyvinyl alcohol, carboxymethylcellulose, lecithin, gelatin, hyaluronic acid and so on. These emulsifiers can be used independently or in combination. The concentration may be selected from the range of about 0.001 to about 20% (w/w). The preferred range is about 0.01 to about 10% (w/w) and the still more preferred range is about 0.05 to about 5% (w/w).

The resultant microcapsules are recovered by centrifugation or filtration and washed with several portions of distilled water to remove the free peptide, vehicle and emulsifier from the surface, then redispersed in distilled water or the like and lyophilized. Then, if necessary, the microcapsules are heated under reduced pressure to further remove the residual water and organic solvent from within the microcapsules. Preferably, this procedure is carried out by heating the microcapsule at a temperature somewhat (5° C. or more) above the median glass transition temperature of the biodegradable polymer as determined with a differential scanning calorimeter at temperature increments of 10° to 20° C./min., generally for not more than 1 week or 2 to 3 days, preferably for not more than 24 hours, after the microcapsules have reached the target temperature.

In the production of microcapsules by the phase separation technique, a coacervation agent is gradually added to a solution of said peptide [I] and biodegradable polymer in an organic solvent with constant stirring so that the biodegradable polymer may separate out and solidify. This coacervation agent is added in a volume of about 0.01 to about 1000 times the volume of the organic solvent solution of peptide [I] and biodegradable polymer. The preferred range is about 0.05 to about 500 times and the still more preferred range is about 0.1 to about 200 times.

The coacervation agent should be a compound of polymer, mineral oil or vegetable oil type which is miscible with the solvent for the biodegradable polymer yet which does not dissolve the polymer. Specifically, silicone oil, sesame oil, soybean oil, corn oil, cottonseed oil, coconut oil, linseed oil, mineral oil, n-hexane, n-heptane, etc. can be mentioned. These substances can be used in combination.

The resultant microcapsules are recovered by filtration and washed repeatedly with heptane or the like to remove the coacervation agent. Then, the free peptide and solvent are removed by the same procedure as described for the drying-in-water technique.

In the drying-in-water technique or in the coacervation technique, an aggregation inhibitor may be added so as to prevent aggregation of particles. The aggregation inhibitor includes water-soluble polysaccharides such as mannitol, lactose, glucose, starch (e.g. corn starch), etc., glycine, proteins such as fibrin, collagen, etc., and inorganic salts such as sodium chloride, sodium hydrogen phosphate and so on.

In the production of microcapsules by the spray drying technique, said organic solvent solution of peptide [I] and biodegradable polymer is ejected in a mist form through a nozzle into the drying chamber of a spray drier to evaporate the organic solvent from the finely-divided liquid droplets in a brief time to provide fine microcapsules. The nozzle may be a two-fluid nozzle, pressure nozzle, rotary disk nozzle and so on. It is advantageous to the process to spray an aqueous solution of said aggregation inhibitor from another nozzle for the prevention of intercapsule aggregation in timed coordination with said spray of the organic solvent solution of peptide [I] and biodegradable polymer.

If necessary, the residual water and organic solvent are removed by heating the resultant microcapsules under reduced pressure in the same manner as described hereinbefore.

The microcapsules can be administered as they are or as processed into various pharmaceutical preparations for administration by routes other than peroral (e.g. intramuscular, subcutaneous and intraorgan injections or implants, nasal, rectal or uterine transmucosal delivery systems, and so on) or for oral administration (e.g. solid preparations such as capsules (e.g. hard capsules, soft capsules, etc.), granules, powders, etc. and liquid preparations such as syrups, emulsions, suspensions and so on).

To process the microcapsules for injection, for instance, the microcapsules can be formulated with a dispersant (e.g. a surfactant such as Tween 80, HCO-60, etc., carboxymethylcellulose, a polysaccharide such as sodium alginate, etc.), a preservative (e.g. methylparaben, propylparaben, etc.), or an isotonizing agent (e.g. sodium chloride, mannitol, sorbitol, glucose, etc.) to prepare an aqueous suspension or they may be dispersed in a vegetable oil such as sesame oil, corn oil or the like to provide an oil suspension for use as a controlled release injection.

The particle size of the microcapsules for such injectable suspensions need only be in the range satisfying the dispersibility and needle passage requirements and may for example range from about 0.1 to about 500 μm. The preferred particle size range is about 1 to about 300 μm and the still more preferred range is about 2 to about 200 μm.

For providing the microcapsules as a sterile product, the whole production process is subjected to sterility control, the microcapsules are sterilized by gamma-ray irradiation or a preservative is added, although these are not exclusive procedures.

Aside from the above-mentioned microcapsules, a biodegradable polymer composition containing the active ingredient peptide well dispersed by a suitable technique can be melted and molded into a spherical, bar-shaped, needle-shaped, pelletized or film shape to provide a sustained-release preparation of the present invention. The above biodegradable polymer composition can be produced by the method described in JP Publication S-50-17525. To be specific, the peptide drug and the polymer are dissolved in a solvent and the solvent is then removed by a suitable method (e.g. spray drying, flash evaporation, etc.) to provide the desired biodegradable polymer composition.

The sustained-release preparation of the present invention can be administered as an intramuscular, subcutaneous or intraorgan injection or implant, a transmucosal delivery system for application to the nasal cavity, rectum or uterus, or an oral preparation (e.g. a solid preparation such as a capsule (e.g. hard or soft), granule, powder, etc. or a liquid preparation such as syrup, emulsion, suspension, etc.).

The sustained-release preparation of the present invention has low toxicity and can be used safely in mammalian animals (e.g. man, bovine, swine, canine, feline, murine, rat and rabbit).

The dosage of the sustained-release preparation is dependent on the type and content of the active drug peptide, final dosage form, the duration of release of the peptide, the object of treatment (such as hormone-dependent diseases, e.g. prostatic cancer, prostatomegaly, endometriosis, metrofibroma, precocious puberty, mammary cancer, etc., or for contraception) and the subject animal species, but in any case it is necessary that an effective amount of peptide is successfully delivered. The unit dosage of the active drug peptide, taking a one-month delivery system as an example, can be selected advantageously from the range of about 0.01 to about 100 mg/kg body weight for an adult human. The preferred range is about 0.05 to about 50 mg/kg body weight. The most preferred range is about 0.1 to about 10 mg/kg body weight.

The unit dosage of the sustained-release preparation per adult human can therefore be selected from the range of about 0.1 to about 500 mg/kg body weight. The preferred range is about 0.2 to about 300 mg/kg body weight. The frequency of administration may range from once in a few weeks, monthly or once in a few months, for instance, and can be selected according to the type and content of the active drug peptide, final dosage form, designed duration of release of the peptide, the disease to be managed and the subject animal.

The following reference and working examples are intended to describe the invention in further detail and should by no means be construed as defining the scope of the invention. (Unless otherwise specified, % means % by weight).

Abbreviations used hereinafter have the following definitions:

BOC: tert-butoxycarbonyl

FMOC: 9-fluorenylmethoxycarbonyl

Cbz: Benzyloxycarbonyl

REFERENCE EXAMPLE 1

A 1000 ml four-necked flask equipped with a nitrogen inlet pipe and condensor was charged with 300 g of 90% aqueous solution of D,L-lactic acid and 100 g of 90% aqueous solution of L-lactic acid and the charge was heated under reduced pressure in a nitrogen gas stream from 100° C./500 mmHg to 150° C./30 mmHg over a period of 4 hours, with the distillate water being constantly removed. The reaction mixture was further heated under reduced pressure at 3–5 mmHg/150°–180° C. for 7 hours, after which it was cooled to provide an amber-colored polylactic acid.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the above polylactic acid were 3,000; 1,790; and 1,297, respectively.

These data showed that the polymer had terminal carboxyl groups.

REFERENCE EXAMPLE 2

A 1000 ml four-necked flask equipped with a nitrogen inlet pipe and condensor was charged with 500 g of 90% aqueous solution of D,L-lactic acid and the charge was heated under reduced pressure in a nitrogen gas stream from 100° C./500 mmHg to 150° C./30 mmHg for a period of 4 hours, with the distillate water being constantly removed. The reaction mixture was further heated under reduced pressure at 3–5 mmHg/150°–180° C. for 12 hours, after which it was cooled to provide an amber-colored polylactic acid.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the above polylactic acid was 5,000; 2,561; and 1,830, respectively.

These data showed that the polymer had terminal carboxyl groups.

REFERENCE EXAMPLE 3

A 1000 ml four-necked flask equipped with a nitrogen inlet pipe and condensor was charged with 300 g of 90% aqueous solution of D,L-lactic acid and 100 g of 90% aqueous solution of L-lactic acid and the charge was heated under reduced pressure in a nitrogen gas stream from 100° C./500 mmHg to 150° C./30 mmHg for a period of 5 hours, with the distillate water being constantly removed. The reaction mixture was further heated under reduced pressure at 5–7 mmHg/150°–180° C. for 18 hours, after which it was cooled to provide an amber-colored polylactic acid.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the above polylactic acid was 7,500; 3,563; and 2,301, respectively.

These data showed that the polymer had terminal carboxyl groups.

REFERENCE EXAMPLE 4

A 1000 ml four-necked flask equipped with a nitrogen inlet pipe and condensor was charged with 300 g of 90% aqueous solution of D,L-lactic acid and 100 g of 90% aqueous solution of L-lactic acid and the charge was heated under reduced pressure in a nitrogen gas stream from 100° C./500 mmHg to 150° C./30 mmHg for a period of 5 hours, with the distillate water being constantly removed. The reaction mixture was further heated under reduced pressure at 5–7 mmHg/150°–180° C. for 26 hours, after which it was cooled to provide an amber-colored polylactic acid.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the above polylactic acid was 9,000; 3,803; and 2,800, respectively.

These data showed that the polymer had terminal carboxyl groups.

REFERENCE EXAMPLE 5

A 1000 ml four-necked flask equipped with a nitrogen inlet pipe and condensor was charged with 182.5 g of glycolic acid and 166.6 g of D,L-2-hydroxybutyric acid and the charge was heated under reduced pressure in a nitrogen gas stream from 100° C./500 mmHg to 150° C./30 mmHg for a period of 3.5 hours, with the distillate water being constantly removed. The reaction mixture was further heated under reduced pressure at 5–7 mmHg/150°–180° C. for 26 hours, after which it was cooled to provide an amber-colored glycolic acid-2-hydroxybutyric acid copolymer.

This polymer was dissolved in 1000 ml of dichloromethane and the solution was poured in warm water at 60° C. with constant stirring. The resulting pasty polymeric precipitates were collected and dried in vacuo at 25° C.

The weight average molecular weight, as determined by GPC, of the resulting glycolic acid-2-hydroxybutyric acid copolymer was 13,000.

REFERENCE EXAMPLE 6

A 1000 ml four-necked flask equipped with a nitrogen inlet pipe and condensor was charged with 197.7 g of glycolic acid and 145.8 g of D,L-2-hydroxybutyric acid and the charge was heated under reduced pressure in a nitrogen gas stream from 100° C./500 mmHg to 155° C./30 mmHg for a period of 4 hours, with the distillate water being constantly removed. The reaction mixture was further heated under reduced pressure at 3–6 mmHg/150°–185° C. for 27 hours, after which it was cooled to provide an amber-colored glycolic acid-2-hydroxybutyric acid copolymer.

This polymer was dissolved in 1000 ml of dichloromethane and the solution was poured in warm water at 60° C. with constant stirring. The resulting pasty polymeric precipitates were collected and dried in vacuo at 25° C.

The weight average molecular weight, as determined by GPC, of the resulting glycolic acid-2-hydroxybutyric acid copolymer was 13,000.

REFERENCE EXAMPLE 7

A 1000 ml four-necked flask equipped with a nitrogen inlet pipe and condensor was charged with 212.9 g of glycolic acid and 124.9 g of D,L-2-hydroxybutyric acid and the charge was heated under reduced pressure in a nitrogen gas stream from 100° C./500 mmHg to 160° C./30 mmHg for a period of 3.5 hours, with the distillate water being constantly removed. The reaction mixture was further heated under reduced pressure at 3–6 mmHg/160°–180° C. for 27 hours, after which it was cooled to provide an amber-colored glycolic acid-2-hydroxybutyric acid copolymer.

This polymer was dissolved in 1000 ml of dichloromethane and the solution was poured in warm water at 60° C. with constant stirring. The resulting pasty polymeric precipitates were collected and dried in vacuo at 25° C.

The weight average molecular weight, as determined by GPC, of the resulting glycolic acid-2-hydroxybutyric acid copolymer was 11,000.

REFERENCE EXAMPLE 8

A 1000 ml four-necked flask equipped with a nitrogen inlet pipe and condensor was charged with 300 g of 90% aqueous solution of D,L-lactic acid and 100 g of 90% aqueous solution of L-lactic acid and the charge was heated under reduced pressure in a nitrogen gas stream from 100° C./500 mmHg to 150° C./30 mmHg for a period of 4 hour with the distillate water being constantly removed. The reaction mixture was further heated under reduced pressure at 3–5 mmHg and 150°–180° C. for 10 hours, after which it was cooled to provide an amber-colored polylactic acid.

This polymer was dissolved in 1,000 ml of dichloromethane and the solution was poured in warm water at 60° C. with constant stirring. The resulting pasty polymeric precipitates were collected and dried in vacuo at 30° C.

The weight-average molecular weight and number average molecular weight, as determined by GPC, and the number average molecular weight, as found by end-group determination, of the above polylactic acid was 4,200; 2,192; and 1,572, respectively.

These data showed that the polymer had terminal carboxyl groups.

REFERENCE EXAMPLE 9

A 1000 ml four-necked flask equipped with a nitrogen inlet pipe and condensor was charged with 182.5 g of glycolic acid and 166.6 g of D,L-2-hydroxybutyric acid and the charge was heated under reduced pressure in a nitrogen gas stream from 100° C./500 mmHg to 150° C./30 mmHg for a period of 3.5-hour, with the distillate water being constantly removed. The reaction mixture was further heated under reduced pressure at 5–7 mmHg and 150°–180°

C. for 32 hours, after which it was cooled to provide an amber-colored glycolic acid, 2-hydroxybutyric acid copolymer.

The polymer was dissolved in 1,000 ml of dichloromethane and the solution was poured in warm water at 60° C. with constant stirring. The resulting pasty polymeric precipitates were collected and dried in a vacuo at 25° C.

The weight-average molecular weight and number average molecular weight, as determined by GPC, and the number average molecular weight, as found by end-group determination, of the resulting glycolic acid.2-hydroxybutyric acid copolymer was 16,300; 5,620; and 2,904, respectively.

These data showed that the polymer had terminal carboxyl groups.

REFERENCE EXAMPLE 10

Synthesis of NAcD2Nal-D4ClPhe-D3Pal-Ser-NMeTyr-DLys(AzaglyFur)-Leu-Lys(Nisp)-Pro-DAlaNH$_2$ Reference Examples 10 and 11 were carried out in accordance with the description of U.S. Pat. No. 5,110,904 and U.S. patent application Ser. No. 07/987,921.

To the reactor of a peptide synthesizer was added 1 g of D-Ala-NH-resin (4-methyl-benzohydrylamine resin), followed by sequential additions of amino acids per the following synthesis procedure, to synthesize the title peptide.

1. Deprotecting reaction

To remove the protecting BOC group from the peptide's alpha amino acid, a solution consisting of 45% trifluoroacetic acid (hereinafter also referred to as TFA), 2.5% anisole, 2.0% dimethyl phosphite and 50.5% dichloromethane was used. After the resin was pre-washed with the solution for 1 minute, a deprotecting reaction was conducted for 20 minutes.

2. Washing with basic solution

To remove and neutralize the trifluoroacetic acid used for deprotection, a dichloromethane solution containing 10% N,N'-diisopropylethylamine was used. The resin was washed for 1 minute three times for each deprotecting reaction.

3. Coupling reaction

A coupling reaction was carried out, using as activators a 3-fold molar amount of 0.3M diisopropylcarbodiimide/dichloromethane solution and a 3-fold molar amount of 0.3M BOC amino acid derivative/DMF (N,N'-dimethylformamide) solution. The activated amino acid was coupled to the free alpha amino group of the peptide on the resin. Reaction times are shown below.

4. Washing

After completion of every reaction process, the resin was washed with dichloromethane, dichloromethane/DMF and DMF, each for 1 minute.

Synthesis protocol

Amino-group-protected amino acids were coupled to the resin in the order, frequency and time shown below.

| Order | Amino acid | Frequency-time |
|---|---|---|
| 1 | BOC-Pro | 2 times–1 hour |
| 2 | BOC-Lys(N-epsilon-Cbz,isopropyl) | 2 times–1 hour |
| 3 | BOC-Leu | 2 times–1 hour |
| 4 | BOC-D-Lys (N-epsilon-FMOC) | 2 times–1 hour |
| 5 | BOC-NMeTyr (O-2,6-diCl-Bzl) | 2 times–1 hour |

-continued

| Order | Amino acid | Frequency-time |
|---|---|---|
| 6 | BOC-Ser(OBzl) | 2 times–1 hour |
| 7 | BOC-D-3Pal | 2 times–6 hours |
| 8 | BOC-D-4ClPhe | 2 times–2 hours |
| 9 | BOC-D2Nal | 2 times–2 hours |
| 10 | Acetic acid | 2 times–2 hours |

After completion of the synthesis reaction, the resin was treated with a 30% piperidine solution in DMF for 4 to 24 hours to remove the protecting FMOC group. The resin was washed with dichloromethane several times and then reacted with carbonyldiimidazole (0.9 g) dissolved in DMF (18 ml) for 15 minutes and washed with dichloromethane three times, after which it was reacted overnight with 2-furoic hydrazide (0.53 g) dissolved in DMF (18 ml). The resulting peptide-resin was washed with dichloromethane three times and then dried in the presence of phosphorus pentoxide overnight, after which it was treated with dry hydrogen fluoride at 0° C. for 1 hour in the presence of anisole to cut the peptide from the resin. The excess reaction reagent was removed under vacuum conditions. The thus-obtained resin was first washed with ether, then stirred at room temperature for 15 minutes in 50 ml of a water/acetonitrile/acetic acid mixture (1:1:0.1) and filtered. The filtrate was lyophilized to yield an unpurified peptide as a fluffy powder. This peptide was purified by high performance liquid chromatography (HPLC) under the following conditions.

(1) Column: Dynamax C-18 (25×2.5 cm, 8 microns)

(2) Solvent: Acetonitrile ascending gradient over a 20-minute period from 89% water/11% acetonitrile/0.1% TFA (3) Detection wavelength: 260 nm (UV method)

The peptide detected as a single peak at 25.7 minutes retention time was collected and lyophilized to yield a purified product of NAcD2Nal-D4ClPhe-D3Pal-Ser-NMeTyr-DLys(AzaglyFur)-Leu-Lys(Nisp)-Pro-DAlaNH$_2$ as a trifluoroacetate. Physical property data on the purified product are as follows:

FAB (fast atom bombardment, the same applies below) mass spectrometry: m/e 1591 (M+H)$^+$ Amino acid analysis: 0.98 Ala, 1.02 Pro, 1.58 Lys, 1.00 Leu, 1.12 NMeTyr, 0.52 Ser The above trifluoroacetate of peptide was converted to an acetate, using a gel filtration column previously equilibrated with 1N acetic acid. Gel filtration conditions are as follows:

(1) Packing: Sephadex G-25 (column inside diameter 16 mm, packing bed height 40 mm)

(2) Solvent: 1N acetic acid (3) Detection wavelength: 254 nm (UV method)

The fraction of the first eluted peak was collected and lyophilized to yield a purified product of NAcD2Nal-D4ClPhe-D3Pal-Ser-NMeTyr-DLys(AzaglyFur)-Leu-Lys (Nisp)-Pro-DAlaNH$_2$ as an acetate.

REFERENCE EXAMPLE 11

Synthesis of NAcD2Nal-D4ClPhe-D3Pal-Ser-NMeTyr-DLys(AzaglyNic)-Leu-Lys(Nisp)-Pro-DAlaNH$_2$ The title peptide was synthesized in the same manner as in Reference Example 10, except that 2-furoic hydrazide was replaced with 2-nicotinic hydrazide (0.575 g). The HPLC retention time of the purified product thus obtained was 16.0 minutes. Physical property data on the purified product are as follows:

FAB mass spectrometry: m/e 1592 (M+H)$^+$

Amino acid analysis: 1.02 Ala, 1.01 Pro, 1.61 Lys, 0.99 Leu, 1.12 NMeTyr, 0.48 Ser The above trifluoroacetate of peptide was converted to an acetate in the same manner as in Reference Example 10.

REFERENCE EXAMPLE 12

A 1000 ml four-necked flask equipped with a nitrogen inlet pipe and condensor was charged with 322 g of 90% aqueous solution of D,L-lactic acid and 133 g of glycolic acid and using a mantle heater (So-go Rikagaku Glass Co.), the charge was heated under reduced pressure in a nitrogen stream from 100° C./500 mmHg to 150° C./30 mmHg for a period of 4 hours the distillate water being constantly removed. The reaction mixture was further heated under reduced pressure at 3–30 mmHg/150°–185° C. for 23 hours, after which it was cooled to provide a lactic acid-glycolic acid copolymer.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the resultant lactic acid-glycolic acid copolymer were 10,000; 4,000; and 4,000, respectively. These data showed that the copolymer was a polymer having terminal carboxyl groups.

REFERENCE EXAMPLE 13

A 1000 ml four-necked flask equipped with a nitrogen inlet pipe and condensor was charged with 347 g of 90% aqueous solution of D,L-lactic acid and 266 g of glycolic acid and using a mantle heater (So-go Rikagaku Glass Co.), the charge was heated under reduced pressure in a nitrogen stream from 100° C./500 mmHg to 150° C./30 mmHg for a period of 5 hours, with the distillate water being constantly removed. The reaction mixture was further heated under reduced pressure at 3–30 mmHg/150°–185° C. for 23 hours, after which it was cooled to provide a lactic acid-glycolic acid copolymer.

This polymer was dissolved in 1000 ml of dichloromethane and the solution was poured in warm water at 60° C. with constant stirring. The resulting pasty polymeric precipitates were collected and dried in vacuo at 30° C.

The weight average molecular weight and number average molecular weight, as determined by GPC, and the number average molecular weight, as found by end-group determination, of the resultant lactic acid-glycolic acid copolymer were 10,000; 3,700; and 3,900, respectively. These data showed that the copolymer was a polymer having terminal carboxyl groups.

EXAMPLE 1

NAcD2Nal-D4ClPhe-D3Pal-Ser-NMeTyr-DLys(Nic)-Leu-Lys(Nisp)-Pro-DAlaNH$_2$ (manufactured by TAP; hereinafter referred to briefly as physiologically active peptide A) acetate, 200 mg, was dissolved in a solution of a 50:50 mixture (3.8 g) of the glycolic acid-2-hydroxybutyric acid copolymer obtained in Reference Example 5 and the polylactic acid obtained in Reference Example 1 in 5.3 g (4.0 ml) of dichloromethane. The resulting solution was cooled to 17° C. and poured into 1000 ml of a 0.1% (w/w) aqueous solution of polyvinyl alcohol (EG-40, Nippon Synthetic Chemical Industry Co., Ltd.) previously adjusted to 10° C. and the mixture was emulsified using a turbine homomixer at 7000 rpm to prepare an O/W emulsion. This O/W emulsion was stirred at room temperature for 3 hours to evaporate the dichloromethane. The oil phase was solidified and collected with a centrifuge (05PR-22, Hitachi, Ltd.) at 2000 rpm. This solid was redispersed in distilled water and further centrifuged to wash off the free drug etc. The collected microcapsules were redispersed in a small quantity of distilled water, followed by addition of 0.3 g of D-mannitol and freeze-drying to provide a powder. The particle size distribution and physiologically active peptide A content of the microcapsules were 5 to 60 μm and 4.7% (w/w), respectively.

Preparations of the following physiologically active peptides (1) and (2) were manufactured in the same manner as above.

(1) NAcD2Nal-D4ClPhe-D3Pal-Ser-NMeTyr-DLys(AzaglyNic)-Leu-Lys(Nisp)-Pro-DAlaNH$_2$ (2) NAcD2Nal-D4ClPhe-D3Pal-Ser-NMeTyr-DLys(AzaglyFur)-Leu-Lys(Nisp)-Pro-DAlaNH$_2$

EXAMPLE 2

In a solution of a 50:50 mixture (3.8 g) of the glycolic acid-2-hydroxybutyric acid copolymer obtained in Reference Example 5 and the polylactic acid obtained in Reference Example 2 in 6.7 g (5.0 ml) of dichloromethane was dissolved 200 mg of physiologically active peptide A acetate. This solution was cooled to 17° C. and poured into 1000 ml of a 0.1% aqueous solution of polyvinyl alcohol previously adjusted to 17° C. and the mixture was treated as in Example 1 to provide microcapsules. The particle size distribution and physiologically active peptide A content of the microcapsules were 5 to 65 μm and 5.0% (w/w), respectively.

EXAMPLE 3

In a solution of a 50:50 mixture (3.8 g) of the glycolic acid-2-hydroxybutyric acid copolymer obtained in Reference Example 5 and the polylactic acid obtained in Reference Example 3 in 6.7 g (5.0 ml) of dichloromethane was dissolved 200 mg of physiologically active peptide A acetate. This solution was cooled to 17° C. and poured into 1000 ml of a 0.1% aqueous solution of polyvinyl alcohol previously adjusted to 17° C. and the mixture was treated as in Example 1 to provide microcapsules. The particle size distribution and physiologically active peptide A content of the microcapsules were 10 to 60 μm and 4.8% (w/w), respectively.

EXAMPLE 4

In a solution of a 50:50 mixture (3.8 g) of the glycolic acid-2-hydroxybutyric acid copolymer obtained in Reference Example 5 and the polylactic acid obtained in Reference Example 4 in 6.7 g (5.0 ml) of dichloromethane was dissolved 200 mg of physiologically active peptide A acetate. This solution was cooled to 17° C. and poured into 1000 ml of a 0.1% aqueous solution of polyvinyl alcohol previously adjusted to 17° C. and the mixture was treated as in Example 1 to provide microcapsules. The particle size distribution and physiologically active peptide A content of the microcapsules were 10 to 75 μm and 4.6% (w/w), respectively.

EXAMPLE 5

In a solution of a 50:50 mixture (3.8 g) of the glycolic acid-2-hydroxybutyric acid copolymer obtained in Reference Example 6 and the polylactic acid obtained in Reference Example 2 in 6.0 g (4.5 ml) of dichloromethane was dissolved 200 mg of physiologically active peptide A acetate. This solution was cooled to 17° C. and poured into 1000 ml of a 0.1% aqueous solution of polyvinyl alcohol previously adjusted to 10° C. and the mixture was treated as in Example 1 to provide microcapsules. The particle size distribution and physiologically active peptide A content of the microcapsules were 5 to 60 μm and 4.9% (w/w), respectively.

EXAMPLE 6

In a solution of a 50:50 mixture (3.8 g) of the glycolic acid-2-hydroxybutyric acid copolymer obtained in Reference Example 7 and the polylactic acid obtained in Reference Example 2 in 6.0 g (4.5 ml) of dichloromethane was dissolved 200 mg of physiologically active peptide A acetate. This solution was cooled to 17° C. and poured into 1000 ml of a 0.1% aqueous solution of polyvinyl alcohol previously adjusted to 17° C. and the mixture was treated as in Example 1 to provide microcapsules. The particle size distribution and physiologically active peptide A content of the microcapsules were 10 to 65 μm and 4.9% (w/w), respectively.

EXAMPLE 7

In a solution of a 50:50 mixture (3.6 g) of the glycolic acid-2-hydroxybutyric acid copolymer obtained in Reference Example 9 and the polylactic acid obtained in Reference Example 8 in 7.0 g (5.3 ml) of dichloromethane was dissolved 400 mg of physiologically active peptide A acetate. This solution was cooled to 17° C. and poured into 1,000 ml of a 0.1% aqueous solution of polyvinyl alcohol previously adjusted to 17° C. and the mixture was treated as in Example 1, to provide microcapsules. The particle size distribution and physiologically active peptide A content of the microcapsules were 5 to 65 μm and 7.2% (w/w), respectively.

EXAMPLE 8

240 mg of the acetate of NAcD2Nal-D4ClPhe-D3Pal-Ser-NMeTyr-DLys(AzaglyNic)-Leu-Lys(Nisp)-Pro-DAlaNH$_2$ (hereinafter referred to briefly as physiologically active peptide B) obtained in Reference Example 11 was dissolved in a solution of a 50:50 mixture (1.76 g) of the glycolic acid.2-hydroxybutyric acid copolymer obtained in Reference Example 9 and the polylactic acid obtained in Reference Example 8 in 3.2 g (2.4 ml) of dichloromethane. The resulting solution was cooled to 18° C. and poured into 400 ml of a 0.1% aqueous solution of polyvinyl alcohol previously adjusted to 16° C. and the mixture was treated as in Example 1, to provide microcapsules. The particle size distribution and physiologically active peptide B content of the microcapsules were 5 to 70 μm and 10.3% (w/w), respectively.

EXAMPLE 9

240 mg of the acetate of NAcD2Nal-D4ClPhe-D3Pal-Ser-NMeTyr-DLys(AzaglyFur)-Leu-Lys(Nisp)-Pro-DAlaNH$_2$ (hereinafter referred to briefly as physiologically active peptide C) obtained in Reference Example 10 was dissolved in a solution of a 50:50 mixture (1.76 g) of the glycolic acid.2-hydroxybutyric acid copolymer obtained in Reference Example 9 and the polylactic acid obtained in Reference Example 8 in 3.2 g (2.4 ml) of dichloromethane. The resulting solution was cooled to 18° C. and poured into 400 ml of a 0.1% aqueous solution of polyvinyl alcohol previously adjusted to 16° C. and the mixture was treated as in Example 1, to provide microcapsules. The particle size distribution and physiologically active peptide C content of the microcapsules were 5 to 65 μm and 10.9% (w/w), respectively.

EXAMPLE 10

N-Tetrahydrofur-2-oyl-Gly-D2Nal-D4ClPhe-D3Pal-Ser-NMeTyr-Dlys(Nic)-Leu-Lys(Nisp)-Pro-DAlaNH$_2$ (Manufactured by TAP; hereinafter referred to briefly as physiologically activepeptide D) acetate [FAB mass spectrometry: m/e 1647 (M+H)$^+$], 240 mg, was dissolved in a solution of a 50:50 mixture (1.76 g) of the glycolic acid-2-hydroxybutyric acid copolymer obtained in Reference Example 9 and the polylactic acid obtained in Reference Example 8 in 3.2 g (2.4 ml) of dichloromethane. The resulting solution was cooled to 18° C. and poured into 400 ml of a 0.1% aqueous solution of polyvinyl alcohol previously adjusted to 16° C. and the mixture was treated as in Example 1 to provide microcapsules. The particle size distribution and physiologically active peptide D content of the microcapsules were 5 to 70 μm and 10.5% (w/w), respectively.

EXAMPLE 11

200 mg of physiologically active peptide A acetate was added and dissolved in a solution of a lactic acid-glycolic acid copolymer (lactic acid/glycolic acid=75/25 (mole %), GPC weight average mol. wt.=5,000, GPC number average mol. wt.=2,000, number average mol. wt. by end-group determination=2,200; manufacturer; Wako Pure Chemical (Lot. 920729)) in 5.3 g (4.0 ml) of dichloromethane. The resulting solution was cooled to 17° C. and poured into 1000 ml of a 0.1% aqueous solution of polyvinyl alcohol (EG-40, Nippon Synthetic Chemical Industry Co., Ltd.) previously adjusted to 16° C. and the mixture was emulsified using a turbine mixer at 7000 rpm to prepare an O/W emulsion. This O/W emulsion was stirred at room temperature for 3 hours to evaporate the dichloromethane. The oil phase was solidified and collected with a centrifuge (05PR-22, Hitachi) at 2000 rpm. This solid was redispersed in distilled water and further centrifuged to wash off the free drug etc. The collected microcapsules were redispersed in a small quantity of distilled water, followed by addition of 0.3 g of D-mannitol and freeze-drying to provide a powder. The particle size distribution and physiologically active peptide A content of the microcapsules were 5 to 60 μm and 4.7% (w/w), respectively.

Sustained-release preparation of the following peptides (1) and (2) are produced in the same manner as above.

(1) Physiologically active peptide B acetate
(2) Physiologically active peptide C acetate

EXAMPLE 12

200 mg of physiologically active peptide A acetate was added and dissolved in a solution of 3.8 g of a lactic acid-glycolic copolymer (lactic acid/glycolic acid=75/25 (mole %), GPC weight average mol. wt.=10,000, GPC number average mol. wt.=4,400, number average mol. wt. by end-group determination=4,300; manufacturer; Wako Pure Chemical (Lot. 880530)) in 6.7 g (5.0 ml) of dichloromethane. The resulting solution was cooled to 17° C. and poured into 1000 ml of a 0.1% aqueous solution of polyvinyl alcohol previously adjusted to 11° C. Thereafter, the procedure of Example 11 was repeated to provide microcapsules. The particle size distribution and physiologically active peptide A content of the microcapsules were 5 to 65 µm and 4.5% (w/w), respectively.

EXAMPLE 13

400 mg of physiologically active peptide A acetate was dissolved in a solution of the lactic acid-glycolic acid copolymer obtained in Reference Example 12, 3.6 g, in 8.0 g (6.0 ml) of dichloromethane. The resulting solution was cooled to 15° C. and poured into 1000 ml of a 0.1% aqueous solution of polyvinyl alcohol previously adjusted to 14° C. Thereafter, the procedure of Example 11 was repeated to provide microcapsules. The particle size distribution and physiologically active peptide A content of the microcapsules were 5 to 65 µm and 8.2% (w/w), respectively.

EXAMPLE 14

400 mg of physiologically active peptide A acetate was dissolved in a solution of the lactic acid-glycolic acid copolymer obtained in Reference Example 13, 3.6 g, in 8.0 g (6.0 ml) of dichloromethane. The resulting solution was cooled to 15° C. and poured into 1000 ml of a 0.1% aqueous solution of polyvinyl alcohol previously adjusted to 15° C. Thereafter, the procedure of Example 11 was repeated to provide microcapsules. The particle size distribution and physiologically active peptide A content of the microcapsules were 5 to 65 µm and 8.4% (w/w), respectively.

EXAMPLE 15

Leuprolerin acetate (manufacturer: Takeda Chemical Industries), 400 mg, was added to a solution of the same lactic acid-glycolic acid copolymer as used in Example 12, 3.6 g, in 8.0 g (60 ml) of dichloromethane to prepare a clear homogeneous solution. The resulting solution was cooled to 15° C. and poured into 1000 ml of a 0.1% aqueous solution of polyvinyl alcohol previously adjusted to 15° C. Thereafter, the procedure of Example 11 was repeated to provide microcapsules.

Experimental Example 1

About 30 mg of the microcapsules obtained in Example 1 were dispersed in a dispersion medium (a solution of 2.5 mg of carboxymethylcellulose, 0.5 mg of polysorbate 80 and 25 mg of mannitol in distilled water) and the dispersion was injected subcutaneously in the back of 10-week-old male SD rats using a 22 G needle (the dosage of microcapsules was 60 mg/kg). Serially after administration, the rats were sacrificed, the remnants of microcapsules were taken out from the administration site and the amount of the physiologically active peptide A in the microcapsules was determined. The results are shown in Table 1.

Experimental Examples 2–6

Using the microcapsules obtained in Examples 2 to 6, the residual amounts of the physiologically active peptide A in the microcapsules were determined as in Experimental Example 1. The results are also shown in Table 1.

TABLE 1

| | Residue of physiologically active peptide A (%) | | | | | | | |
|---|---|---|---|---|---|---|---|---|
| | Day 1 | Week 1 | Week 2 | Week 3 | Week 4 | Week 5 | Week 6 | Week 8 |
| Experimental Example 1 | 88.0 | 66.5 | 42.3 | 15.2 | | | | |
| Experimental Example 2 | 92.8 | 76.6 | 62.6 | 48.7 | 38.6 | 26.5 | | |
| Experimental Example 3 | 96.5 | 90.5 | 77.5 | 64.9 | 59.2 | 46.9 | 38.7 | 20.3 |
| Experimental Example 4 | 99.4 | 94.5 | 87.2 | 76.3 | 66.0 | — | 46.6 | 30.7 |
| Experimental Example 5 | 92.9 | 75.0 | 45.7 | — | 17.5 | | | |
| Experimental Example 6 | 92.3 | 61.3 | 33.5 | 6.4 | | | | |

It is apparent from Table 1 that all the microcapsules according to the present invention are characterized by substantially constant release of physiologically active peptide and are further characterized by being substantially free from an initial burst.

Table 2 shows the linear regression models, correlation coefficients, and release periods calculated as X-intercept which were determined by the procedures described in Methods of Bioassay (authored by Akira Sakuma, Tokyo University Press, Jun. 5, 1978, p. 111).

TABLE 2

| | Weight average molecular weight of polylactic acid | Linear regression model | Correlation coefficient | Release period (weeks) |
|---|---|---|---|---|
| Experimental Example 1 | 3000 | Residue (%) = 95.4-(26.9 × no. of weeks) | ($R^2$ = 0.992) | 3.5 |
| Experimental Example 2 | 5000 | Residue (%) = 94.4-(14.2 × no. of weeks) | ($R^2$ = 0.975) | 6.6 |
| Experimental Example 3 | 7500 | Residue (%) = 98.4-(10.0 × no. of weeks) | ($R^2$ = 0.996) | 9.8 |
| Experimental Example 4 | 9000 | Residue (%) = 102.1.-(8.9 × no. of weeks) | ($R^2$ = 0.995) | 11.5 |

It is apparent from Table 2 that by varying the weight average molecular weight of polylactic acid to be blended with glycolic acid-2-hydroxybutyric copolymer, the duration of release can be freely controlled within the range of about 3.5 weeks to about 11.5 weeks.

Table 3 shows the linear regression models, correlation coefficients and release periods as X-intercept which were determined from the data in Table 1 by the same procedures as used in Table 2.

TABLE 3

| | Mole fraction of glycolic acid in glycolic acid copolymer | Linear regression model | Correlation coefficient | Release period (weeks) |
|---|---|---|---|---|
| Experimental Example 2 | 60% | Residue (%) = 94.4-(14.2 × no. of weeks) | ($R^2$ = 0.975) | 6.6 |

TABLE 3-continued

| | Mole fraction of glycolic acid in glycolic acid copolymer | Linear regression model | Correlation coefficient | Release period (weeks) |
|---|---|---|---|---|
| Experimental Example 5 | 65% | Residue (%) = 95.7-(20.6 × no. of weeks) | ($R^2$ = 0.976) | 4.6 |
| Experimental Example 6 | 70% | Residue (%) = 96.6-(30.9 × no. of weeks) | ($R^2$ = 0.994) | 3.1 |

It is apparent from Table 3 that by varying the mole fraction of glycolic acid in the glycolic acid-2-hydroxybutyric acid copolymer to be blended with polylactic acid, the duration of release can be freely controlled within the range of about 3.1 weeks to about 6.6 weeks.

Experimental Examples 7–9

Using the microcapsules obtained in Examples 7 to 9, the residual amounts of the physiologically active peptide in the microcapsules were determined as in Experimental Example 1, except that the microcapsule dose was about 30 mg/kg. The results are shown in Table 4. Table 5 shows the linear regression models, correlation coefficients and release periods calculated as X-intercepts, which were determined from the data in Table 4 by the same procedure as used in Table 2.

TABLE 4

| | Physiologically active | Residue of Physiologically active peptide (%) | | | | |
|---|---|---|---|---|---|---|
| | | 1 Day | 1 Week | 2 Weeks | 3 Weeks | 4 Weeks |
| Experimental Example 7 | A | 99.3 | 74.5 | 51.4 | 33.2 | 24.1 |
| Experimental Example 8 | B | 87.4 | 75.0 | 52.3 | 32.8 | 25.1 |
| Experimental Example 9 | C | 89.4 | 73.6 | 54.9 | 37.7 | 23.4 |

TABLE 5

| | Physiologically active Peptide | regression model | Correlation Coefficient | Release period (weeks) |
|---|---|---|---|---|
| Experimental Example 7 | A | Residue (%) = 97.8-(20.1 × no. of weeks) | ($R^2$ = 0.975) | 4.9 |
| Experimental Example 8 | B | Residue (%) = 93.5-(18.6 × no. of weeks) | ($R^2$ = 0.971) | 5.0 |
| Experimental Example 9 | C | Residue (%) = 94.4-(18.5 × no. of weeks) | ($R^2$ = 0.987) | 4.9 |

It is apparent from Tables 4 and 5 that the microcapsules according to the present invention are characterized by substantially constant release of physiologically active peptide and are further characterized by being substantially free from an initial burst.

Experimental Example 10

Using the microcapsules obtained in Example 10, the residual amounts of the physiologically active peptide in the microcapsules were determined as in Experimental Example 7. The results are shown in Table 6. Table 7 shows the linear regression models, correlation coefficients and release periods calculated as X-intercepts, which were determined from the data in Table 6 by the same procedure as used in Table 2.

TABLE 6

| | Residue of physiologically active peptide D (%) | | | | |
|---|---|---|---|---|---|
| | Day 1 | Week 1 | Week 2 | Week 3 | Week 4 |
| Experimental Example 10 | 93.5 ± 0.5 | 69.9 ± 3.6 | 37.3 ± 1.6 | 17.0 ± 1.4 | 7.9 ± 0.5 |

TABLE 7

| | Linear regression model | Correlation coefficient | Release periods (weeks) |
|---|---|---|---|
| Experimental Example 10 | Residue (%) = 95.0 - (24.1 × no. of weeks) | ($R^2$ = 0.969) | 3.9 |

It is apparent from Tables 6 and 7 that the microcapsules according to the present invention are characterized by substantially constant release of physiologically active peptide and are further characterized by being substantially free from an initial burst.

Experimental Example 11

About 30 mg of the microcapsules obtained in Example 11 were dispersed in 0.5 ml of a dispersion medium (prepared by dissolving carboxymethylcellulose (2.5 mg), polysorbate 80 (0.5 mg) and mannitol (25 mg) in distilled water) and, the dispersion was injected subcutaneously at the back of 10-week-old male SD rats using a 22 G needle (the dosage as microcapsules 60 mg/kg). Serially after administration, the rats were sacrificed, the remains of microcapsules were taken out from the administration site and the amount of the physiologically active peptide A in the microcapsules was determined. The results are shown in Table 8.

Experimental Example 12

Using the microcapsules obtained in Example 12, the procedure of Experimental Example 11 was otherwise repeated and the residue of physiologically active peptide A was assayed. The results are shown in Table 8.

Experimental Example 13

Using the microcapsules obtained in Example 13, the procedure of Experimental Example 11 was otherwise repeated and the residue of physiologically active peptide A was assayed. The results are shown in Table 8.

Experimental Example 14

Using the microcapsules obtained in Example 14, the procedure of Experimental Example 11 was otherwise repeated and the residue of physiologically active peptide A was assayed. The results are shown in Table 8.

TABLE 8

| | Residue of physiologically active peptide A (%) | | | | | | |
|---|---|---|---|---|---|---|---|
| | Day 1 | Week 1 | Week 2 | Week 3 | Week 4 | Week 6 | Week 8 |
| Experimental Example 11 | 82.8 | 21.8 | — | — | — | — | — |
| Experimental Example 12 | 96.7 | 91.7 | 79.5 | 69.2 | 59.2 | — | 22.8 |
| Experimental Example 13 | 100.0 | 84.3 | 43.9 | 31.9 | — | — | — |
| Experimental Example 14 | 96.3 | 67.5 | 38.0 | 23.5 | — | — | — |

(—: not determined)

Table 9 shows the linear regression models, correlation coefficients, and release periods as X-intercept which were determined from the data in Table 8 by the same procedures as used in Table 2.

TABLE 9

| | Linear regression model | Correlation coefficient | Release periods (weeks) |
|---|---|---|---|
| Experimental Example 11 | Residue (%) = 97.1 - (75.7 × no. of weeks) | ($R^2$ = 0.994) | 1.3 |
| Experimental Example 12 | Residue (%) = 92.2 - (9.7 × no. of weeks) | ($R^2$ = 0.998) | 10.3 |
| Experimental Example 13 | Residue (%) = 102.4 - (24.8 × no. of weeks) | ($R^2$ = 0.982) | 4.1 |
| Experimental Example 14 | Residue (%) = 97.7 - (26.5 × no. of weeks) | ($R^2$ = 0.989) | 3.7 |

It is apparent from Tables 8 and 9 that the sustained-release preparation according to the present invention invariably insure a substantially constant release of the peptide over various segments of the time.

Comparative Example 1

400 mg of physiologically active peptide A acetate was added to a solution of a lactic acid-glycolic acid copolymer ((lactic acid/glycolic acid=50/50 (mole %), GPC weight average mol. wt.=58,000, GPC number average mol. wt.= 14,000, number average mol. wt. by end-group determination=45,000; manufacturer; Boehringer-Ingelheim (Lot. RG505-05077), 3.6 g, in 33.2 g (25.0 ml) of dichloromethane but the physiologically active peptide A acetate could not be successfully dissolved.

Comparative Example 2

400 mg of physiologically active peptide A acetate was added to a solution of lactic acid-glycolic acid copolymer (lactic acid/glycolic acid=75/25 (mole %), GPC weight average mol. wt.=18,000, GPC number average mol. wt.= 8,400, number average mol. wt. by end-group determination=30,000; manufacturer; Boehringer-Ingelheim (Lot. RG752-15057), 3.6 g, in 8.0 g (6.0 ml) of dichloromethane but the physiologically active peptide A could not be successfully dissolved. This dispersion was cooled to 17° C. and poured into 1,000 ml of a 0.1% aqueous solution of polyvinyl alcohol previously adjusted to 15° C. to prepare microcapsules in the same manner as in Example 11. The particle size distribution and physiologically active peptide A content of the microcapsules were 10 to 90 µm and 2.5% (w/w), respectively.

Comparative Example 3

400 mg of physiologically active peptide A acetate, was added to a solution of lactic acid-glycolic acid copolymer (lactic acid/glycolic acid=75/25 (mole %), GPC weight average mol. wt.=58,000, GPC number average mol. wt.= 15,000, number average mol. wt. by end-group determination=53,000; manufacturer; Boehringer-Ingelheim (Lot. RG755-05019), 3.6 g, in 21.2 g (16.0 ml) of dichloromethane but the physiologically active peptide A could not be successfully dissolved. This dispersion was cooled to 17° C. and poured into 1,000 ml of a 0.1% aqueous solution of polyvinyl alcohol previously adjusted to 16° C. to prepare microcapsules in the same manner as in Example 11. The particle size distribution and physiologically active peptide A content of the microcapsules were 10 to 90 µm and 3.6% (w/w), respectively.

As shown in Comparative Examples 1 to 3, with a lactic acid-glycolic acid copolymer having substantially no terminal carboxyl group, the peptide [I] of the present invention could not be successfully dissolved.

Comparative Example 4

Leuprolerin acetate (manufacturer: Takeda Chemical Industries), 400 mg, was added to a solution of the same lactic acid-glycolic acid copolymer as used in Comparative Example 2, 3.6 g, in 8.0 g (6.0 ml) of dichloromethane but the leuprolerin acetate could not be successfully dissolved.

The sustained-release preparation of the present invention shows a constant release of the drug, especially the peptide [I] over a long time, thus being conducive to a lasting and stable effect. Furthermore, the duration of release of the drug can be easily controlled and excessive release immediately following administration can be inhibited. Specifically the histamine-releasing activity in the peptide [I] following administration of the sustained-release preparation is inhibited. The sustained-release preparation has excellent dispersibility. Moreover, the preparation is stable (e.g. to light, heat, humidity, colouring) and of low toxicity and, therefore, can be safely administered.

In accordance with the production method of the present invention, a sustained-release preparation containing a physiologically active peptide can be easily obtained in good yield. The thus obtained sustained-release preparation has a smooth surface and is excellent in mobility.

What is claimed is:

1. A method for treating a luteinizing hormone-dependent disease or a follicle stimulating hormone-dependent disease in a mammal which comprises administering to a mammal in need thereof a therapeutically effective amount of a sustained-release preparation comprising a physiologically active peptide of the following formula:

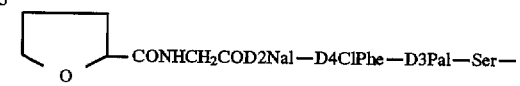

—NMeTyr—DLys(Nic)—Leu—Lys(Nisp)—Pro—DAlaNH$_2$ or an acetate salt thereof, and a biodegradable polymer having a terminal carboxyl group.

2. A method for antagonizing LH-RH activity in a mammal which comprises administering to a mammal in need thereof a therapeutically effective amount of a sustained-release preparation comprising a physiologically active peptide of the following formula:

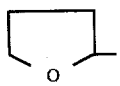—CONHCH$_2$COD$_2$Nal—D4ClPhe—D3Pal—Ser—

—NMeTyr—DLys(Nic)—Leu—Lys(Nisp)—Pro—DAlaNH$_2$ or an acetate salt thereof, and a biodegradable polymer having a terminal carboxyl group.

3. A method for antagonizing LH-RH activity in a mammal which comprises administering to a mammal in need thereof a therapeutically effective amount of a sustained-release preparation comprising a physiologically active peptide of the following formula:

—CONHCH$_2$COD$_2$Nal—D4ClPhe—D3Pal—Ser—

—NMeTyr—DLys(Nic)—Leu—Lys(Nisp)—Pro—DAlaNH$_2$ or an acetate salt thereof, and a biodegradable polymer having a terminal carboxyl group prior to administering LH-RH agonist to the mammal.

4. A sustained-release preparation for treating a hormone-dependent diseases comprising an effective amount of a physiologically active peptide of the following formula:

—CONHCH$_2$COD2Nal—D4ClPhe—D3Pal—Ser—

—NMeTyr—DLys(Nic)—Leu—Lys(Nisp)—Pro—DAlaNH$_2$ or an acetate salt thereof, and a biodegradable polymer having a terminal carboxyl group.

5. A sustained-release preparation for antagonizing LH-RH activity comprising an effective amount of a physiologically active peptide of the following formula:

—CONHCH$_2$COD2Nal—D4ClPhe—D3Pal—Ser—

—NMeTyr—DLys—(Nic)—Leu—Lys(Nisp)—Pro—DAlaNH$_2$ or an acetate salt thereof, and a biodegradable polymer having a terminal carboxyl group.

6. A method for treating a gonad-derived steroid hormone-dependent disease in a mammal which comprises administering to a mammal in need thereof a therapeutically effective amount of a sustained-release preparation comprising a physiologically active peptide of the following formula:

—CONHCH$_2$COD2Nal—D4ClPhe—D3Pal—Ser—

—NMeTyr—DLys(Nic)—Leu—Lys(Nisp)—Pro—DAlaNH$_2$ or an acetate salt thereof, and a biodegradable polymer having a terminal carboxyl group.

* * * * *